US012527921B2

(12) United States Patent
Cherif-Cheikh et al.

(10) Patent No.: US 12,527,921 B2
(45) Date of Patent: Jan. 20, 2026

(54) PASSIVE INJECTION DEVICE WITH AUTOMATIC SECURING MEANS

(71) Applicant: EDIX SA, Luxembourg (LU)

(72) Inventors: Roland Cherif-Cheikh, Castelldefels-Barcelona (ES); Tabatha Bourgois, Barcelona (ES); Lluis Pareta Beltran, Castellbisball-Barcelona (ES); Frederic Lacombe, Sant Cugat del Valles (ES); Laurence Lachamp, Gava Barcelona (ES)

(73) Assignee: EDIX SA, Luxembourg (LU)

( * ) Notice: Subject to any disclaimer, the term of this patent is extended or adjusted under 35 U.S.C. 154(b) by 1043 days.

(21) Appl. No.: 17/285,656

(22) PCT Filed: Oct. 15, 2019

(86) PCT No.: PCT/EP2019/077993
§ 371 (c)(1),
(2) Date: Apr. 15, 2021

(87) PCT Pub. No.: WO2020/079012
PCT Pub. Date: Apr. 23, 2020

(65) Prior Publication Data

US 2021/0393889 A1 Dec. 23, 2021

(30) Foreign Application Priority Data

Oct. 16, 2018 (FR) ...................................... 1859566

(51) Int. Cl.
*A61M 5/32* (2006.01)
*A61M 5/28* (2006.01)
(Continued)

(52) U.S. Cl.
CPC .......... *A61M 5/3287* (2013.01); *A61M 5/283* (2013.01); *A61M 5/31501* (2013.01);
(Continued)

(58) Field of Classification Search
CPC .............. A61M 5/282; A61M 5/31505; A61M 5/5066; A61M 5/326; A61M 5/3287;
(Continued)

(56) References Cited

U.S. PATENT DOCUMENTS 4,852,768 A * 8/1989 Bartsch ................. G01F 11/027 222/34
2003/0212362 A1* 11/2003 Roser .................... A61M 5/282 604/110
(Continued)

FOREIGN PATENT DOCUMENTS

WO 2004/032989 4/2004
WO 2015/048791 4/2015

OTHER PUBLICATIONS

International Search Report for PCT/EP2019/077993 dated Jan. 17, 2020, 9 pages.
(Continued)

*Primary Examiner* — Michael J Tsai
*Assistant Examiner* — Justin L Zamory
(74) *Attorney, Agent, or Firm* — NIXON & VANDERHYE

(57) ABSTRACT

Disclosed is an injection device of the type including a cylindrical body enclosing a reservoir containing a product to be injected, which is slidably mounted in the body, which is open at one end on an injection needle and is closed at its other end by a plunger mounted movable in translation in the reservoir under the action of a plunger rod provided with a control member, the surface of the distal end of the body being coated with adhesive capable of ensuring that this surface is held on the skin of a patient. This device is characterized in that it includes a mechanism for securing
(Continued)

the needle, the activation of which is ensured by the adhesive when a withdrawal effort is exerted on the injection device.

13 Claims, 4 Drawing Sheets

(51) Int. Cl.
*A61M 5/315* (2006.01)
*A61M 25/02* (2006.01)

(52) U.S. Cl.
CPC .... *A61M 5/31511* (2013.01); *A61M 5/31578* (2013.01); *A61M 5/3202* (2013.01); *A61M 2025/0266* (2013.01)

(58) Field of Classification Search
CPC .............. A61M 5/283; A61M 5/31501; A61M 5/31511; A61M 5/31578; A61M 5/3202; A61M 5/281; A61M 5/42; A61M 5/3234; A61M 5/3232
See application file for complete search history.

(56) References Cited

U.S. PATENT DOCUMENTS

2004/0199112 A1* 10/2004 Dalton .................. A61M 5/326 604/110
2009/0227942 A1* 9/2009 Stroem Hansen ...... A61M 5/30 604/116

OTHER PUBLICATIONS

Written Opinion of the ISA for PCT/EP2019/077993 dated Jan. 17, 2020, 8 pages.
French Search Report for FR 1859566 dated Jun. 21, 2019, 2 pages.
English translation of the International Preliminary Report issued for PCT/EP2019/077993 dated Apr. 14, 2021.

* cited by examiner

PASSIVE INJECTION DEVICE WITH AUTOMATIC SECURING MEANS

CROSS-REFERENCE TO RELATED APPLICATIONS

This application is the U.S. national phase of International Application No. PCT/EP2019/077993 filed Oct. 15, 2019 which designated the U.S. and claims priority to FR 1859566 filed Oct. 16, 2018, the entire contents of each of which are hereby incorporated by reference.

BACKGROUND OF THE INVENTION

Field of the Invention

The present invention relates to a passive safety injection device intended to allow increased stability of its positioning during the injection and a total and automatic protection of its injection needle before, during and after the injection.

Description of the Related Art

Such a safety device is said to be passive because, on the one hand, its operation is entirely independent of the way in which the user operates to carry out the injection and, on the other hand, the user cannot carry out operations or errors that would prevent it from being triggered, such as, for example, not completing an injection before removing the needle.

By full needle protection is meant that the needle can be maintained in an aseptic or sterile environment without external contact until it is implanted at the injection site.

Such a passive safety injection device can be applied to all injection devices and in particular to conventional syringes with smooth plunger rod activated in translation.

It can also be applied to injection devices with screw, with a threaded plunger rod activated in rotation.

It is also known that for medical and nursing specialists, an injection is done by translation, while for the general population, this gesture is much less common, natural and simple than rotation.

In fact, translational injection is an atypical gesture that is never performed in everyday life, this gesture requiring precise positioning of three fingers.

This translation can give the patient the impression of introducing something into his body by moving the thumb under pressure towards the skin.

This gesture performed without a fixed support poses a problem of stability which causes movements of the implanted needle and hinders the accuracy of the dosages. This gesture is sensitive to the pressure received in return, which can be perceived as variable, which therefore makes it difficult to perform at a constant speed from start to finish. Finally, in this unstable holding position, pauses during the injection depending on the pain felt are difficult to achieve.

The injection in rotation is a usual gesture carried out daily in the everyday life, which can be carried out without precise positioning with different fingers, or even with the hand.

This rotation avoids the impression of introducing something into your body and drastically reduces the pressure on the skin. This gesture is performed with a fixed support which stabilizes the device and the needle, is not sensitive to pressure and is naturally performed at constant speed. In this stable holding position, pauses on the basis of perception are easy to achieve.

Another constraint linked to injections, especially when the latter are carried out by non-specialists and involve viscous or pasty products, is to know when the entire dose has been injected. Faced with this uncertainty, the tendency is to press very hard at the end of the injection, causing pain by the pressure and the movements of the needle in the tissues.

In addition, with injections in translation, the visibility of the plunger at the bottom of the syringe reservoir very close to the injection point is always difficult, whereas with injections in rotation, it is impossible to force in pressure and one can present a precise and visible stopping point of the rotation which signals the end of the injection.

In addition, the graduations can be placed higher on the body of the device where they are much easier to read than at the base, in contact with the skin.

In the case of self-injectors in translation by pressure, these devices exert a strong pressure on the skin, hardly compatible and poorly tolerated by the patients, especially for children and the elderly for whom this represents a real sensation of a blow or a shock.

SUMMARY OF THE INVENTION

The present invention aims to provide a means for stabilizing the distal part of an injector device which comes into contact with the skin of a patient to be treated, such stabilization favoring the use of an injection device by rotation of a control member. Of course, such a stabilization means is also advantageous for the implementation of any other injection device, in particular by translation.

The present invention also aims to provide an injection device by rotation requiring only one hand of the user to implement it.

Furthermore, with regard to safety, injection devices are known which are provided with mechanisms allowing, once the injection operation is completed, to retract the injection needle inside the body of the device, which thus avoids any risk of accidental needle sticking to the user.

However, injection devices of this type which, most of the time, make use of spring mechanisms, turn out to be of great complexity which generally results in high cost prices.

Thus, patent applications US 2003/212362 and WO 2004/032989 disclose injection devices whose stability is ensured on the body of a patient by means of adhesive means arranged on their distal end and which also comprise means making it possible to ensure safety of the needle after the injection.

Such systems are made up of complex mechanical means which have the disadvantage of using elements likely to generate jolts during the administration of the products to be injected, which may exert stresses on the needle introduced into the patient's body, which may cause injury and pain for the patient.

Finally, document WO 2015/048791 discloses an injection device capable of optionally having adhesive means on its distal part making it possible to ensure its stabilization on the skin of a patient.

However, such a device does not have passive means making it possible to automatically ensure protection of the syringe throughout and after the injection phase.

The present invention aims to provide a safety injection device which is simple and consequently easier and less expensive to produce and which, moreover, does not present the risk of injuring the patient during the injection.

The object of the present invention is thus an injection device of the type comprising a cylindrical body enclosing a reservoir containing a product to be injected, which is slidably mounted in the body, which is open at one end on an injection needle and which is closed at its other end by a plunger mounted so as to be movable in translation in the reservoir under the action of a plunger rod provided with a control member, the surface of the distal end of the body being coated with adhesive means capable of ensuring that this surface is held on the skin of a patient, characterized in that it comprises means for securing the needle, the activation of which is ensured by the adhesive means when a withdrawal force is exerted on the injection device.

The control member may consist of a cylindrical cap which will be mounted to slide on the body, the plunger rod being secured by its proximal end to the bottom of this cap and passing through an element mounted movable in translation in the cap.

This movable element may consist of a nut in which the plunger rod will be screwed or of a drawer in which the plunger rod will be slidably mounted.

The proximal end of the reservoir may be secured to said element and may include at least one deformable tab which will extend towards the bottom of the cap and terminate in a radial boss extended by a bevel.

Furthermore, the distal face of the element may include a circular groove of a shape complementary to that of the bevel of the deformable tab so as to receive the latter when the element is applied against the proximal face of the body and to deform it in the direction of the longitudinal axis of the latter.

The internal face of the cap may include a first proximal circular stop, the distal face of which will be perpendicular to the axis of the body, and a second distal circular stop of rectangular section perpendicular to the axis of the body.

The height of the circular stops may be such that, when the element is applied against the proximal face of the body, the deformation of the tab will allow the passage of the radial boss at its level when the cap is moved relative to the body.

This height of the circular stops may be such that, when the element is not applied against the proximal face of the body, the tab will be released and its radial boss will come into abutment against the distal face of the proximal circular abutment and in abutment against the proximal face of the distal circular stop when moving the cap relative to the body.

According to the invention, in the rest position, or not in use, the distal surface of the body coated with the adhesive means may be protected by a removable membrane.

The present invention also aims to an injection device of the type comprising a cylindrical body enclosing a reservoir containing a product to be injected, which is open at one end on an injection needle and is closed at its other end by a mounted plunger movable in translation in the reservoir under the action of a control member, characterized in that the surface of the distal end of the body is extended by a boss.

This boss may be of planar shape and substantially perpendicular to the longitudinal axis of the body or be of convex shape.

BRIEF DESCRIPTION OF THE DRAWINGS

An embodiment of the present invention will be described below, by way of non-limiting example, with reference to the appended drawing in which.

DESCRIPTION OF THE PREFERRED EMBODIMENTS

FIGS. 1 to 5 show an implementation of an injection device according to the invention of the type in which the injection is performed by means of rotation.

This injection device 1 comprises a tubular body 3 which is hollowed out of an axial cylindrical duct 5 which opens into a cylindrical distal chamber 7 of larger diameter.

Figure 1:
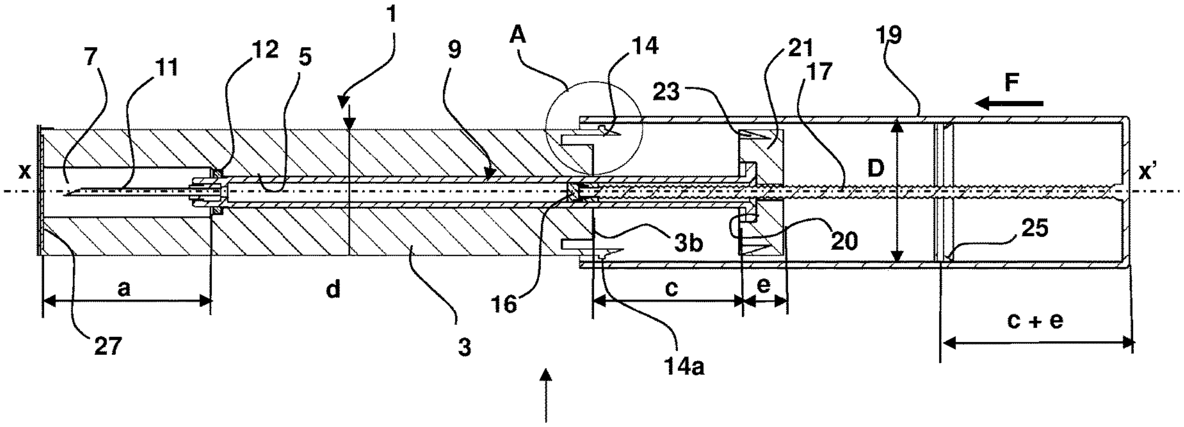
FIG. 1 is a view in axial and longitudinal section of an embodiment of an injection device according to the invention shown in the rest or pre-injection position.
Figure 1A:
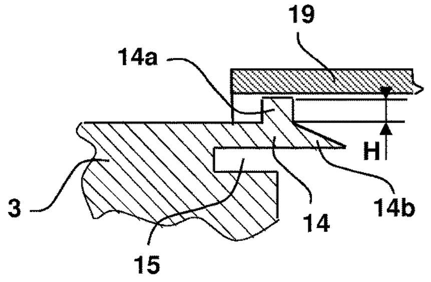
FIG. 1*a* is an enlarged view of zone A of the injection device as shown in FIG. 1.
Figure 3A:
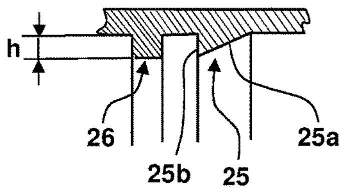
FIG. 3*a* is an enlarged view of zone B of the injection device as shown in FIG. 3.

The conduit 5 receives a reservoir, constituted in this embodiment, by a syringe 9 containing the product to be injected which ends with an injection needle 11. The distal end of the syringe 9 is provided with an O-ring seal 12 which is recessed in a cuvette 10 of the body 3, and the length a of the chamber 7 is such, that in the rest position, or pre injection, as shown in FIG. 1, the injection needle 11 is housed inside the chamber 7.

The proximal end 3*b* of the body 3 ends with two diametrically opposed hooking tabs 14 which themselves end in an external boss 14*a* of height H followed by a bevel 14*b*, these tabs being made deformable by the presence of an internal space 15.

A plunger 16 is slidably mounted inside the syringe 9 under the action of a threaded plunger rod 17. The proximal end of this plunger rod is integral with the bottom of an actuating member consisting of a cylindrical cap 19 whose internal diameter D is slightly greater than that d of the body 3 increased by the height H of the two stops 14*a*, so as to allow the cap 19 to slide on the body 3. We thus have D=d+2×H. In the rest position, as shown in FIG. 1, the distal end of this cap 19 is slightly engaged on the body 3 so as to favour the guiding of the latter.

The internal face of the cap 19 comprises a first circular distal stop 26 of height h, of rectangular cut, aiming to keep the body 3 locked in the cap 19 during the withdrawal of the needle from the body 4 once the administration of the product is finished. Finally, the internal face of the cap also comprises a second circular proximal stop 25 of height h, the proximal face 25*a* of which is preferably inclined and the distal face 25*b* is radial, and spaced from the first stop 25 by a distance equal to the width of the boss 14*a*, and which is intended, as explained below, to prevent a second exit of the needle 11 once the injection phase is finished.

A cylindrical nut 21 of thickness e forming a stop is screwed onto the plunger rod 17 and comprises a cup 20 in which the proximal end of the syringe 9 is fixed. The periphery of the distal face of the nut 21 is hollowed out by a circular groove 23 of a shape complementary to that of the bevel 14*b* of the deformable tabs 14. The diameter b of this nut 21 is slightly less than the internal diameter D of the cap 19 from which the heights H of the two bosses 14*a* have been subtracted. We thus have b=D−2×H.

The distance c which exists, when the injection device is at rest, as shown in FIG. 1, between the proximal end 3*b* of the body 3 and the distal face of the nut 21 allows to control the distance of which the injection needle 11 will emerge from the distal face 3*a* of the body 3 during the injection, as explained below.

Figure 2:
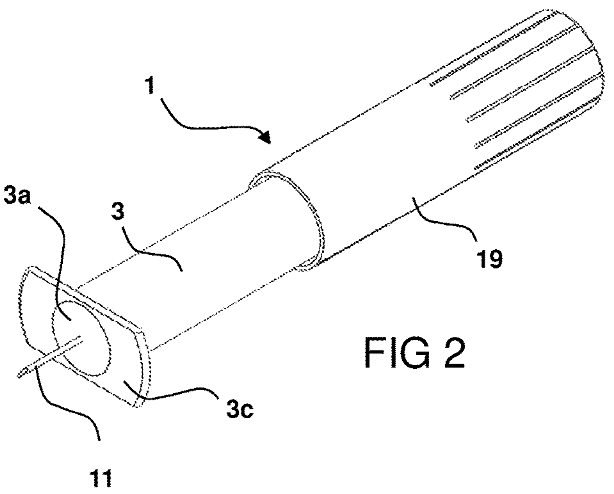
FIG. 2 is a perspective view of the injection device shown in FIG. 1 before the injection phase.

This distal face 3*a* of the cylindrical body 3 can be formed by the annular surface of the body 3 or, as in the embodiment shown in FIG. 2, include an extension part 3*c* plane and perpendicular to the longitudinal axis xx' of the injection device, allows to increase the size of this surface.

According to the invention, the latter is coated with an adhesive capable of allowing adhesion with the skin 4 of the patient to be treated, this adhesive being protected in the position of non-use, by a pellicle or a film 27.

For example, use will be made of adhesive surfaces based on silicone, acrylate, polyacrylates, or any other known copolymers entering into the adhesive surface composition for medical devices, such as for example dressings, ostomy bags, electrodes and electrosurgical plates, patches or even hair prostheses.

Figure 10:
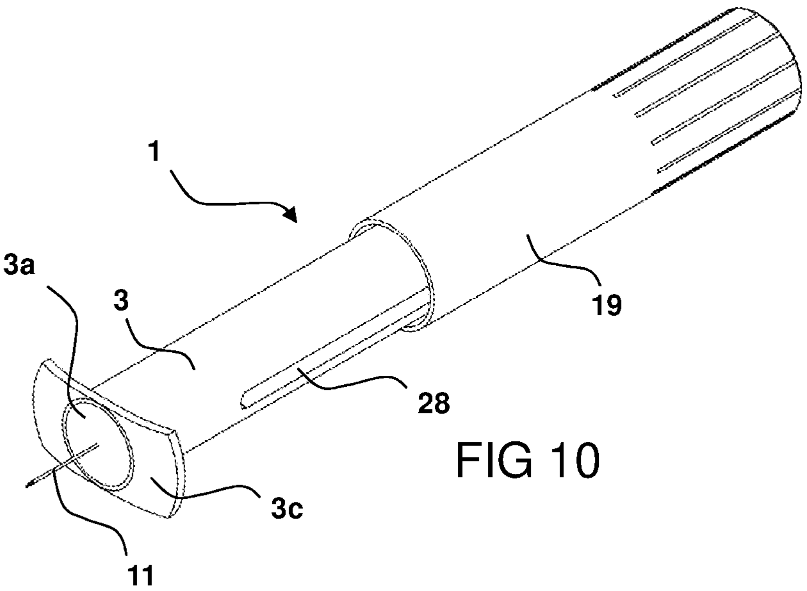
FIG. 10 is an alternative embodiment of the injection device according to the invention.

In an alternative embodiment, the extension part 3*c* may be non-planar and in particular be of convex shape as shown in FIG. 10.

Thus, during the implantation of the needle in the patient's body, the deformation of the surface of the skin by depression will adapt better to the whole of the sticky surface, adhere better to it and better fix the device to his injection site.

At the end of the injection, a simple movement perpendicular to the surface of the skin around the needle will allow the injection device to be withdrawn, thus avoiding rocking movements liable to move the needle in the body. This perpendicular withdrawal will also facilitate the detachment of this adhesive surface: the skin located further on the periphery of said adhesive surface will peel off first and thus gradually to the part closest to the needle.

This non-planar sticky surface, which avoids the detachment of the entire surface at the same time after injection, increases the strength of the bond without making its removal difficult or painful. This upward and progressive movement of the skin at the time of the withdrawal of the needle also avoids the usual bleeding at the injection site linked to a phenomenon of suction of the needle in the opening that it made in the tissues. By pulling the skin back when the needle is withdrawn, this sticky surface system compensates for this phenomenon of suction and ensures that the opening closes without causing blood resurgence.

It will be noted that in the injection device according to the invention, the adhesive surface has two functions.

A first function, known from the prior state of the art, is to stabilize the injection device with respect to the patient's skin so as to prevent any slippage during the injection phase.

A second function, as explained in detail below, is to control the activation of a safety mechanism of the injection device when the user exerts a pulling force on it to remove it from the patient's body, thus making this safety automatic, without the user having to perform any additional action.

Under these conditions, the operation of the injection device according to the invention is established as described below.

After removing the protective film 27, the user brings the adhesive distal end of the injection device into contact with the area of the patient's body, where he wishes to perform the injection. Therefore this end of the injection device, due to its adhesion with the injection zone, is stabilized.

Figure 3:
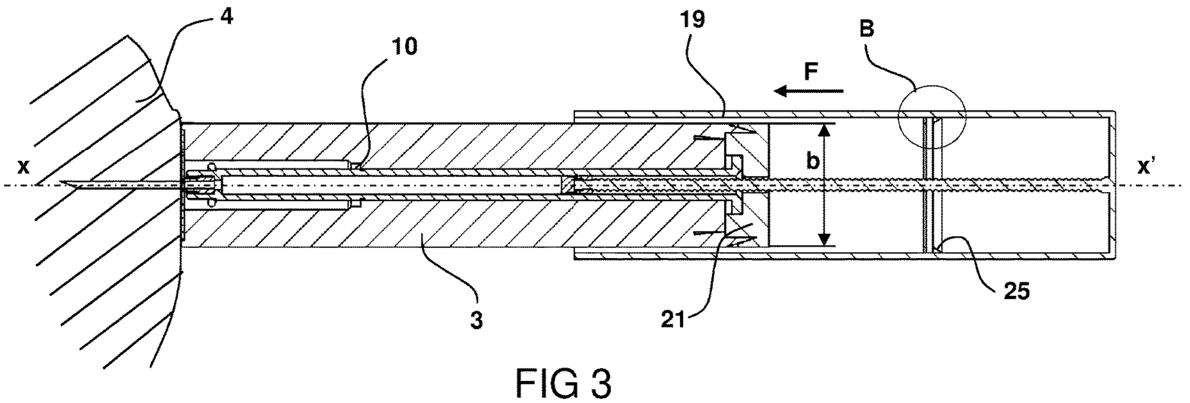
FIG. 3 is an axial and longitudinal sectional view of the injection device of FIG. 1 shown in progress injection.

Then, the user exerts a linear push on the cap 19 in the direction of the arrow F until the nut 21 comes into abutment with the proximal face 3*b* of the body 3, which has the effect on the one hand of making the injection needle 11 come out of the injection device and introduce it into the body 4 of the patient, as shown in FIG. 3. On the other hand, at the end of this translation movement, the bevels 14*b* of the tongues 14 penetrate into the groove 23 of the nut 21, which has the effect of deforming the tongues 14 inwards and ensuring a rotational connection of the nut 21 with the body 3. Moreover, due to the inward deformation of the tongues, they are free and able to avoid blocking the cap's movement when, during injection, they reach the circular stops 25 and 26.

The injection device is therefore ready to proceed with the injection of the treatment product.

To do this, the user rotates the cap 19, which he can moreover perform with one hand due to the connection existing between the distal part 3*a* of the body 3 with the body 4 of the patient which is ensured. by the adhesive product.

Figure 4:
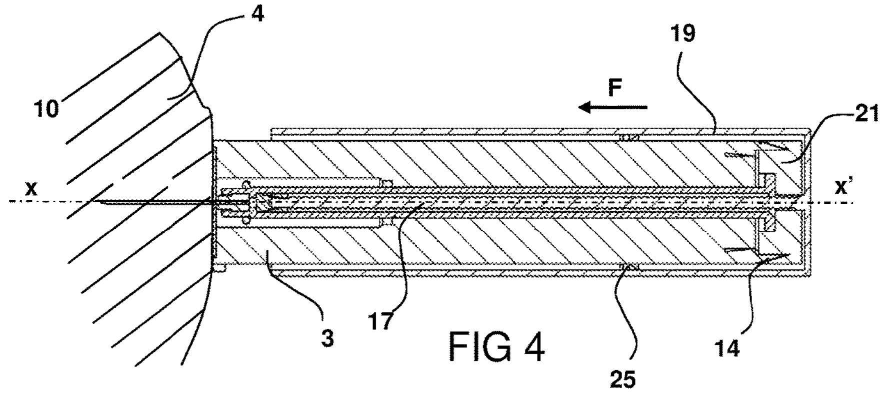
FIG. 4 is an axial and longitudinal sectional view of the injection device of FIGS. 1 and 3 shown once the injection completed.

During this rotation of the cap 19, the plunger rod 17 is screwed into the nut 21, and the latter being immobilized in rotation with respect to the body 3, the plunger 16 moves in the syringe 9 and administers the treatment product in the patient's body until the plunger reaches the syringe neck 9, as shown in FIG. 4, or the user stops his injection.

Once the injection has been carried out, the user pulls the cap 19 in the opposite direction of the arrow F. During this movement of withdrawal of the injection device, the distal face 3*a* thereof being held in adhesion. with the skin of the patient, the nut 21 is brought back so that the tabs 14 are then released and return to their initial position.

Figure 5:
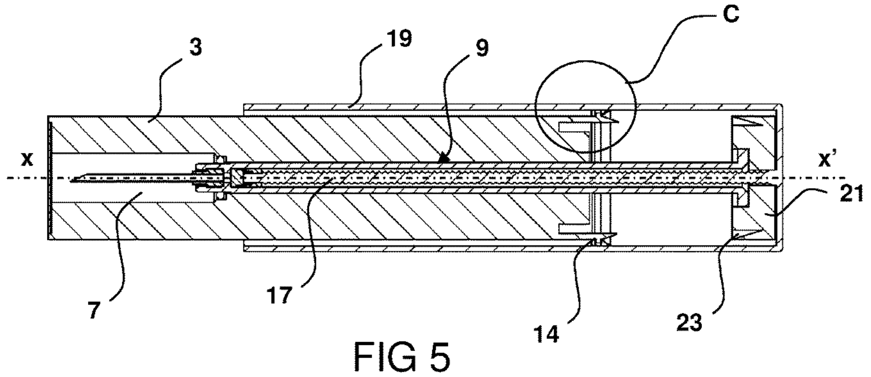
FIG. 5 is a view in axial and longitudinal section of the injection device of FIGS. 1 to 4 shown after injection once placed in the safety position.
Figure 5A:
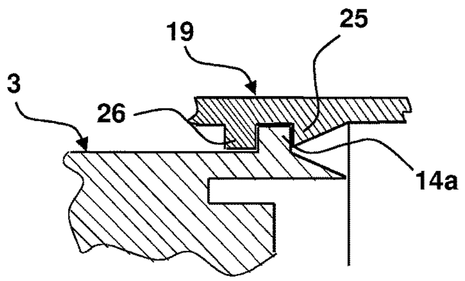
FIG. 5*a* is an enlarged view of zone C of the injection device as shown in FIG. 5.

The withdrawal movement takes place until the proximal face 25*a* of the stop 25 comes into contact with the boss 14*a* and the latter falls into the free space between the two stops 25 and 26 as shown in the FIGS. 5 and 5*a*.

Consequently, any relative movement of the cap 19 with respect to the body 3 in the direction of arrow F or in the opposite direction is no longer possible and the injection device is thus locked and secured against any subsequent use.

It is understood under these conditions that it is the second function exerted by the means for bonding the distal end of the injection device to the patient's skin which has the effect of controlling the actuation of the safety device during the withdrawal phase.

Such an arrangement is particularly advantageous for several reasons.

Firstly, it makes it possible to produce a safety injection device in a particularly simple manner compared to the prior devices of the state of the art which make use of complex mechanisms and which, consequently, are particularly difficult to manufacture. which makes them more expensive.

Secondly, this arrangement makes it possible to trigger the means capable of ensuring the safety of the injection device by a withdrawal movement thereof, unlike previous devices in which the safety is obtained by a pressure movement on the patient's body that occurs in an area near the injection site. However, we know that this kind of pressure is likely to cause the risk of bleeding or bruising.

By continuing the withdrawal movement, the user ensures the detachment of the distal face of the injection device from the surface of the patient's skin thanks to the blocking of the body 3 with respect to the cap 19 against the second distal stop 26.

Of course, although the present example is described with respect to a small volume syringe, in particular of the insulin type, it can be adapted to any other device using standard or non-standard syringes or cartridges, either according to a rotation-controlled injection mode as described in the present example or according to translation-controlled injection modes with conventional syringes using smooth plunger rods and finger supports.

In such a version with a smooth plunger rod actuated in translation, the cap 19 could be replaced by two arms also integral with the plunger rod. These two arms could circulate in two windows inside the finger support.

As for the screw version, the needle would be implanted by pushing these two arms in the direction of arrow F.

Moreover, the safety means implemented in the present injection device also have the advantage of being able to replace the cap which usually covers the injection needle. This eliminates an operation of removing the cap which is dangerous because it exposes the user to the cutting bevel, and also it can damage the injection needle and that finally it involves risks of external contaminations of this needle before it is injected.

In an alternative embodiment of the invention and as shown in FIG. 10, the body 3 may include a window 28 which will extend along the syringe and which will make it possible to check its contents before use.

Furthermore, and according to the invention, a label may connect the body 3 to the cap 19 so as to ensure the relative retention of these two parts before the injection. Such a label will also allow to verify the integrity of the injection device seal before use. This label may include a precut line promoting its breakage during injection.

Of course, the passive injection device with automatic safety according to the invention is not limited to the mechanisms described above and could be applied to any other type of mechanism in which the function of triggering the safety means would be ensured by gluing its distal part to the patient's skin.

The present invention could for example be applied in particular to an injection device in which the injection would be carried out not by rotation, as described above, but by translation.

FIGS. 6 to 9 show such an injection device for which the notations and references used in the previous example will be kept.

This injection device has the following essential differences with the previous device.

First of all, it comprises a plunger rod 17' which consists of a smooth, unthreaded rod which is slidably mounted in an axial bore of a drawer 21' with a level of friction $f_1$. The drawer 21' is mounted in the cap 19 so that it can move in translation with the lowest possible friction level $f_0$.

This drawer has at its proximal end a circular groove 23 of the same type as that of the nut 21 of the previous example.

Under these conditions, the operation of the injection device according to the invention is established as described below.

Figure 6:
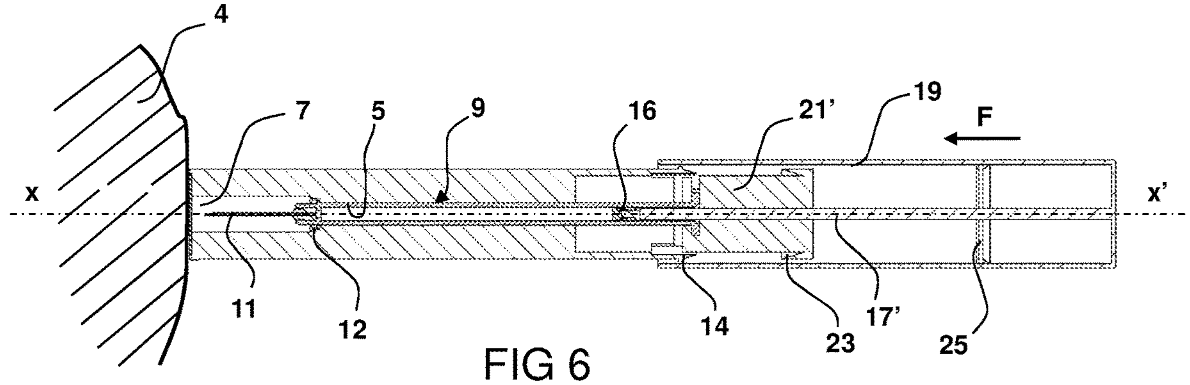
FIGS. 6 to 9 show a second embodiment of an injection device according to the invention, in which the injection is carried out by translation means, respectively in the rest position, during injection, at the end of the injection and in the safety position.

As before, and as shown in FIG. 6, after removing the protective film 27, the user brings the adhesive distal end of the injection device into contact with the area of the patient's body, where he wishes to perform the injection. Therefore this end of the injection device, due to its adhesion with the injection zone, is stabilized.

Figure 7:
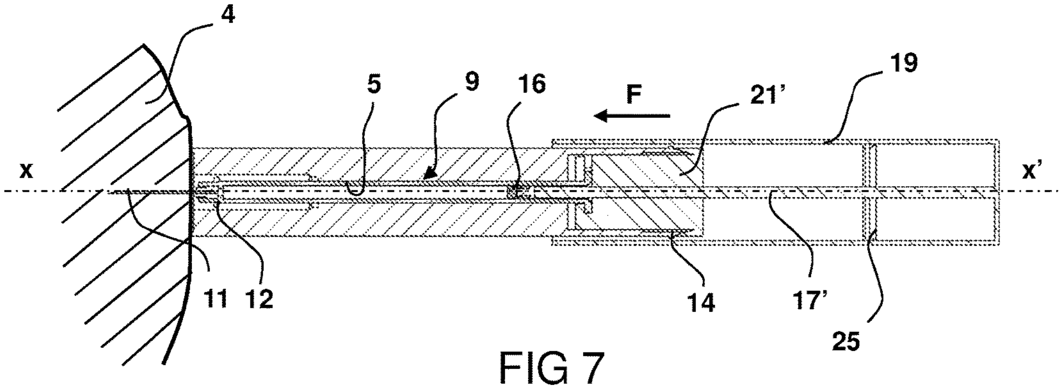

Then, starting from the rest position shown in FIG. 6 and as shown in FIG. 7, the user exerts a linear thrust on the cap 19 in the direction of arrow F. It will also be noted that one will do so that the level of friction $f_1$ is greater than the level of friction $f_2$ necessary for the deformation of the tabs 14 by the circular groove 23 of the drawer 21' plus the level of friction $f_3$ between the O-ring 12 and the body of the syringe 9. We will thus have: $f_1>f_2+f_3$ Under these conditions, the translational movement exerted on the cap 19 has the first effect of causing the injection needle 11 to come out of the injection device and to introduce it into the body 4 of the patient, as shown in FIG. 7. On the other hand, at the end of this translational movement, the bevels 14*b* of the tabs 14 penetrate into the groove 23 of the drawer 21', which has the effect of deforming the tabs 14 inwardly as was the case in the previous example.

The injection device is therefore ready to proceed with the injection of the treatment product.

Figure 8:
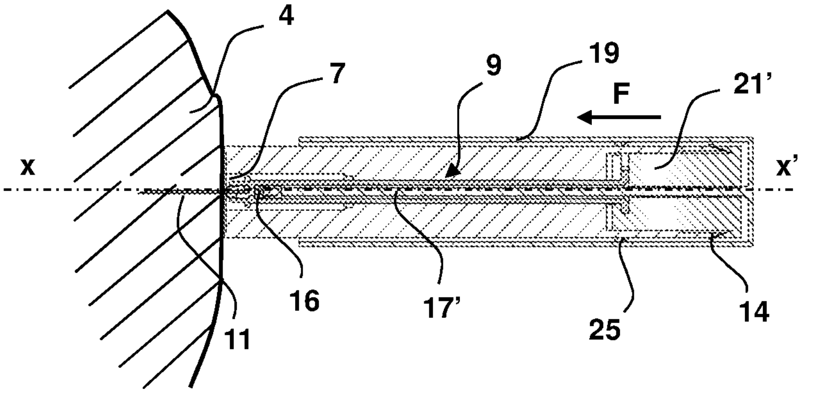
Figure 9:
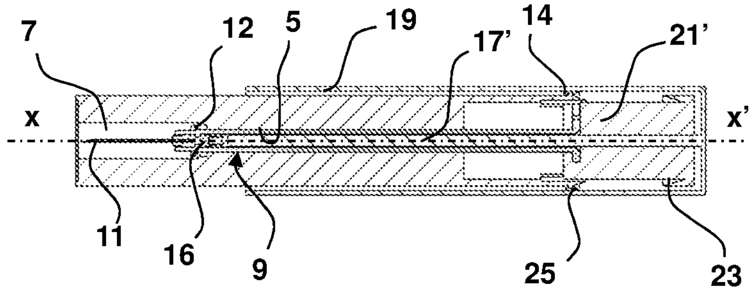

To do this, the user continues his axial displacement movement in the direction of arrow F so that the plunger 16 moves in the syringe 9 and administers the treatment product in the patient's body until the plunger reaches the neck of the syringe 9, as shown in FIG. 8, or that the user stops his injection.

Once the injection has been carried out, the user pulls on the cap 19 in the opposite direction to the arrow F. From then on, the injection means are made safe as described above.

The invention claimed is:

1. An injection device comprising a cylindrical body (3) enclosing a reservoir (9) containing a product to be injected, which is slidably mounted in the body (3), which is open at one end on an injection needle (11) and is closed at another end by a plunger (16) mounted so as to be movable in translation in the reservoir under the action of a plunger rod (17) provided with a control member comprising a cylindrical cap (19) which is slidably mounted on the body (3), the plunger rod (17) being secured by a proximal end to the bottom of this cap (19) and passing through an element mounted so as to be movable in translation in the cap, the movable element comprising a nut (21) into which the plunger rod (17) is screwed, the cap being moved axially to engage the nut and then rotated to deliver the dose, the surface of the distal end (3*a*) of the body (3) being coated with adhesive means capable of ensuring that this surface is held on the skin (4) of a patient wherein the injection device comprises means for securing the needle in a retracted position within said cylindrical body after use, the activation of said securing means being ensured by the adhesive means when a withdrawal effort is exerted on the injection device while the distal end (3*a*) of the body (3) is maintained on the skin (4) of a patient by said adhesive means, said injection device being free of a spring mechanism.

2. The injection device according to claim 1 wherein the movable element consists of a drawer (21') in which the plunger rod (17') is slidably mounted.

3. The injection device according to claim 1 wherein the proximal end of the reservoir (9) is secured to the element (21, 21').

4. The injection device according to claim 1 wherein the proximal end (3*b*) of the body (3) comprises at least one deformable tab (14) which extends towards the bottom of the cap (19) and ends with a radial boss (14*a*) extended by a bevel (14*b*).

5. The injection device according to claim 4 wherein the distal face of the element (21, 21') comprises a circular groove (23) of a shape complementary to that of the bevel (14*b*) of the deformable tab (14) so as to receive the deformable tab when the element (21, 21') is applied against the proximal face (3*b*) of the body (3) and to deform the deformable tab in the direction of the longitudinal axis (xx') of the body.

6. The injection device according to claim 5 wherein the internal face of the cap (19) comprises a first proximal circular stop (25), the distal face (25*b*) of which is perpendicular to the axis (xx') of the body (3), and a second distal circular stop (26) of rectangular cross-section perpendicular to the axis (xx') of the body (3).

7. The injection device according to claim 6 wherein the height (H) of the circular stops (25, 26) is such that, when the element (21, 21') is applied against the proximal face (3*b*) of the body (3), the deformation of the tab (14) allows the passage of the radial boss (14*a*) at their level during a displacement of the cap (19) relative to the body (3).

8. The injection device according to claim 7 wherein the height (H) of the circular stops (25, 26) is such that, when the element (21, 21') is not applied against the proximal face (3*b*) of the body (3), the tab (14) is released and the radial boss (14*a*) abuts against the distal face of the proximal circular stop (25) and stops against the proximal face of the distal circular stop (26) when moving the cap (19) relative to the body (3).

9. The injection device according to claim 1 wherein, in the rest position, or not in use, the distal surface (3*a*) of the body (3) which is coated with adhesive means is protected by a removable membrane.

10. The injection device comprising a cylindrical body (3) enclosing a reservoir (9) containing a product to be injected according to claim 1, which is open at one end on an injection needle (11) and is closed at another end by a plunger (16) mounted so as to be able to move in translation in the reservoir under the action of a control member (19) wherein the surface of the distal end (3*a*) of the body (3) is extended by a boss (3*c*).

11. The injection device according to claim 10 wherein the boss (3*c*) is of planar shape and substantially perpendicular to the longitudinal axis (xx') of the body (3).

12. The injection device according to claim 10 wherein the boss (3c) is of convex shape.

13. The injection device according to claim 2 wherein the proximal end of the reservoir (9) is secured to the element (21, 21').

* * * * *